United States Patent
Shi et al.

(10) Patent No.: US 11,872,058 B2
(45) Date of Patent: Jan. 16, 2024

(54) MEDICAL IMAGING SYSTEM AND TEST BED FOR SAME

(71) Applicant: GE Precision Healthcare LLC, Wauwatosa, WI (US)

(72) Inventors: Jinkai Shi, Beijing (CN); Wende Li, Beijing (CN); Zhihan Li, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 771 days.

(21) Appl. No.: 16/899,694

(22) Filed: Jun. 12, 2020

(65) Prior Publication Data

US 2020/0405178 A1    Dec. 31, 2020

(30) Foreign Application Priority Data

Jun. 28, 2019    (CN) .......................... 201921010905.1

(51) Int. Cl.
| | |
|---|---|
| *A61B 5/055* | (2006.01) |
| *A61B 5/00* | (2006.01) |
| *G01G 19/44* | (2006.01) |
| *G01G 19/52* | (2006.01) |

(52) U.S. Cl.
CPC ............ *A61B 5/704* (2013.01); *A61B 5/0033* (2013.01); *A61B 5/742* (2013.01); *G01G 19/445* (2013.01); *G01G 19/52* (2013.01); *A61B 2562/0252* (2013.01); *A61B 2562/225* (2013.01)

(58) Field of Classification Search
CPC ....... A61B 5/055; A61B 5/0033; A61B 5/704; A61B 2562/0252; G01G 19/445; G01G 19/52
See application file for complete search history.

(56) References Cited

U.S. PATENT DOCUMENTS

| | | | | |
|---|---|---|---|---|
| 4,926,951 | A | * | 5/1990 | Carruth ................ G01G 19/445 177/144 |
| 4,974,692 | A | * | 12/1990 | Carruth .................. G01G 21/06 177/144 |
| 5,823,278 | A | * | 10/1998 | Geringer ................ G01G 19/52 177/144 |
| 5,861,582 | A | * | 1/1999 | Flanagan ............. G01G 19/445 177/144 |
| 2009/0252300 | A1 | * | 10/2009 | Schwartz ................ A61B 5/055 378/209 |
| 2010/0287703 | A1 | * | 11/2010 | Zapata .................. A61B 6/5276 5/607 |
| 2013/0146371 | A1 | | 6/2013 | Shih |
| 2017/0003159 | A1 | * | 1/2017 | Kostic .................. G01G 19/445 |

* cited by examiner

*Primary Examiner* — Fredrick C Conley (57) ABSTRACT

The present utility model provides a test bed, a magnetic resonance imaging system, and a medical imaging system. The test bed includes a support frame used to bear a tested object, a base used to support the support frame, and at least one weighing assembly. The at least one weighing assembly is fixed to the base, and acquires weight information of the tested object by sensing stress from the support frame.

16 Claims, 8 Drawing Sheets

MEDICAL IMAGING SYSTEM AND TEST BED FOR SAME

CROSS-REFERENCE TO RELATED APPLICATIONS

This application claims the benefit of Chinese Patent Application No. 201921010905.1 filed on Jun. 28, 2019, the disclosure of which is herein incorporated by reference in its entirety.

TECHNICAL FIELD

The present utility model relates to the medical field, and in particular to a medical imaging system and a test bed for the same.

BACKGROUND

In a Magnetic Resonance Imaging (Magnetic Resonance Imaging, MRI) system, in a uniform intense magnetic field generated by a magnet, the precession frequency of protons in an organism is determined by field strength and is consistent. If a linear gradient magnetic field is additionally added to a main magnetic field, then because the precession frequency of proton groups in different parts of a tested object may be different due to different magnetic induction intensity, nuclear magnetic resonance imaging can be performed on a certain part of the tested object. Therefore, during scanning performed on the tested object, scanning time and scanning intensity need to be determined according to the weight of the tested object.

During actual operation, generally weight information of a patient needs to be acquired by means of a weight scale provided outside a scanning room or by means of face-to-face inquiry. However, it is difficult to weigh a patient incapable of standing by means of a weight scale. Further, some patients do not know their own weight.

SUMMARY

The present utility model provides a test bed, a magnetic resonance imaging system, and a medical imaging system.

An exemplary embodiment of the present utility model provides a test bed. The test bed comprises a support frame used to bear a tested object, a base used to support the support frame, and at least one weighing assembly, wherein the at least one weighing assembly is fixed to the base and acquires weight information of the tested object by sensing stress from the support frame.

Specifically, the weighing assembly comprises a sensor unit used to sense the stress from the support frame. Further, the weighing assembly further comprises a force transmission apparatus used to transmit the stress from the support frame to the sensor unit, and the force transmission apparatus is mounted on an upper side of the sensor unit. Further, the weighing assembly further comprises a fixing apparatus used to fix and support the sensor unit; the fixing apparatus is mounted on a lower side of the sensor unit; a deformation space is formed in a position on the lower side of the sensor unit opposite the force transmission apparatus; and the deformation space allows the sensor unit to deform along the direction of the stress. Further, the sensor unit is a single-ended beam load cell.

Specifically, the test bed comprises a plurality of weighing assemblies, and the plurality of weighing assemblies are fixed between the support frame and an upper surface of the base. Further, the test bed comprises four weighing assemblies symmetrical about a center, and the center is the center of gravity of the support frame.

Specifically, the base further comprises a movement assembly provided at the bottom of the base, and the weighing assembly is fixed to the movement assembly. Further, the movement assembly comprises two movement wheels positioned at one end of the bottom of the base and two movement wheels positioned at the other end of the bottom of the base; the test bed comprises two weighing assemblies; and each weighing assembly is fixed to two adjacently positioned movement wheels. Further, the weighing assembly comprises two sensor units, and the sensor units are respectively fixed to the movement wheels.

An exemplary embodiment of the present utility model provides a medical imaging system. The medical imaging system comprises the aforementioned test bed and a control apparatus.

Specifically, the control apparatus further comprises a connection unit; the connection unit is connected to at least one weighing assembly; the at least one weighing assembly comprises at least one sensor unit; the connection unit is used to receive a measurement signal sent by the at least one sensor unit. Further, the connection unit comprises an adjustable resistor module, and the resistance of the adjustable resistor module is changed so that a weighing parameter of the at least one sensor unit is changed.

Specifically, the control apparatus further comprises a processing unit, and the processing unit is connected to the connection unit and used to perform calculation on a measurement value from the connection unit so as to acquire weight information of a tested object.

Specifically, the control apparatus further comprises a display unit, and the display unit is connected to the processing unit and used to display the weight information of the tested object.

An exemplary embodiment of the present utility model further provides a magnetic resonance imaging system. The magnetic resonance imaging system comprises a main magnet and the aforementioned test bed.

Specifically, the magnetic resonance imaging system comprises a connection unit; the connection unit is connected to at least one weighing assembly in the test bed; the at least one weighing assembly comprises at least one sensor unit; the connection unit is used to receive a measurement signal sent by the at least one sensor unit. Further, the connection unit is positioned away from the main magnet. Further, the connection unit is provided at an end of the test bed located away from the main magnet.

Other features and aspects will become clear through the following detailed description, accompanying drawings, and claims.

BRIEF DESCRIPTION OF THE DRAWINGS

The present utility model may be better understood by describing exemplary embodiments of the present utility model with reference to accompanying drawings, in which.

DETAILED DESCRIPTION

Specific implementation manners of the present utility model will be described in the following. It should be noted that during the specific description of these implementation manners, it is impossible to describe all of the features of the actual implementation manners in detail in this description for the sake of brief description. It should be understood that in the actual implementation of any one of the implementation manners, as in the process of any engineering project or design project, a variety of specific decisions are often made in order to achieve the developer's specific objectives and meet system-related or business-related restrictions, which will vary from one implementation manner to another. Moreover, it can also be understood that although the efforts made in such development process may be complex and lengthy, for those of ordinary skill in the art related to content disclosed in the present utility model, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present utility model pertains. The words "first," "second" and similar words used in the description and claims of the patent application of the present utility model do not denote any order, quantity, or importance, but are merely intended to distinguish between different constituents. "One," "a" and similar words are not meant to be limiting, but rather denote the presence of at least one. The word "include," "comprise," or a similar word is intended to mean that an element or article that appears before "include" or "comprise" encompasses an element or article and equivalent elements that are listed after "include" or "comprise," and does not exclude other elements or articles. The word "connect," "connected," or a similar word is not limited to a physical or mechanical connection, and is not limited to a direct or indirect connection.

Figure 1:
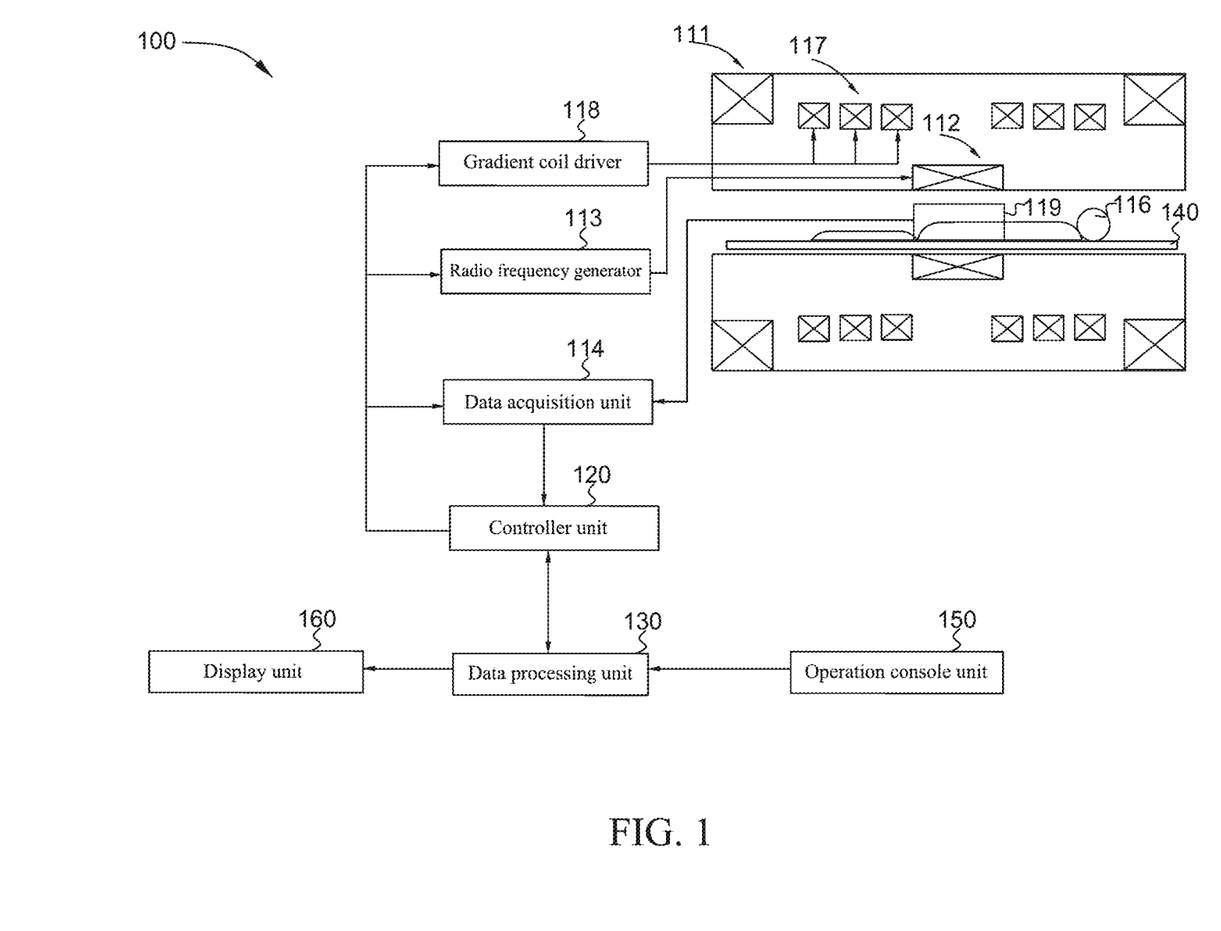
FIG. 1 is a schematic diagram of a magnetic resonance system according to some embodiments of the present utility model.

FIG. 1 shows a schematic diagram of an MRI system 100 according to some embodiments of the present invention. As shown in FIG. 1, the MRI system 100 includes a scanner 110, a controller unit 120, and a data processing unit 130. The MRI system 100 is described only as an example. In other embodiments, the MRI system 100 may have a plurality of transformations, as long as image data can be acquired from a tested object.

The scanner 110 may be used to acquire data of the tested object 116. The controller unit 120 is coupled to the scanner 110 and is used to control operation of the scanner 110. The scanner 110 may include a main magnet 211, a radio frequency transmit coil 112, a radio frequency generator 113, a gradient coil system 117, a gradient coil driver 118, and a radio frequency receive coil 119.

The main magnet 111 generally includes, for example, an annular superconducting magnet, where the annular superconducting magnet is mounted in an annular vacuum container. The annular superconducting magnet defines a cylindrical space surrounding the tested object 116. Moreover, a constant static magnetic field, such as a static magnetic field B0, is generated along a Z direction of the cylindrical space. The MRI system 100 uses the formed static magnetic field B0 to emit a magnetostatic pulse signal to the tested object 116 placed in an imaging space, so that the precession of protons in the body of the tested object 116 is ordered to generate a longitudinal magnetization vector.

The radio frequency generator 113 is used to generate a radio frequency pulse. The radio frequency pulse may include a radio frequency excitation pulse. The radio frequency excitation pulse is amplified (by, for example, a radio frequency power amplifier, not shown), and is then applied to the radio frequency transmit coil 112, so that the radio frequency transmit coil 112 emits to the tested object 116 a radio frequency magnetic field B1 orthogonal to the static magnetic field B0 so as to excite nuclei in the body of the tested object 116, and the longitudinal magnetization vector is converted into a transverse magnetization vector. After the end of the radio frequency excitation pulse, a free induction decay signal (i.e., a magnetic resonance signal that can be acquired) is generated in the process that the transverse magnetization vector of the tested object 116 is gradually restored to zero.

The radio frequency transmit coil 112 may be a body coil, and the body coil may be connected to a transmit/receive (T/R) switch (not shown). The transmit/receive switch is controlled so that the body coil can be switched between a transmit mode and a receive mode. In the receive mode, the body coil may be used to receive the magnetic resonance signal from the tested object 116.

The gradient coil system 117 forms a gradient magnetic field in the imaging space so as to provide three-dimensional position information for the magnetic resonance signal. The magnetic resonance signal may be received by the radio frequency receive coil 119 or the body coil in the receive mode. The data processing unit 130 may process the received magnetic resonance signal so as to acquire the required image or image data.

Specifically, the gradient coil system 117 may include three gradient coils. Each of the three gradient coils generates a gradient magnetic field inclined to one of three spatial axes (for example, X-axis, Y-axis, and Z-axis) perpendicular to each other, and generates a gradient field according to imaging conditions in each of a slice selection direction, a phase encoding direction, and a frequency encoding direction. More specifically, the gradient coil system 117 applies a gradient field in the slice selection direction of the tested object 116 so as to select a slice. The radio frequency transmit coil 112 emits the radio frequency excitation pulse to the slice selected by the tested object 116 and excites the slice. The gradient coil system 117 also applies a gradient field in the phase encoding direction of the tested object 116 so as to perform phase encoding on a magnetic resonance signal of the excited slice.

The gradient coil system 117 then applies a gradient field in the frequency encoding direction of the tested object 116 so as to perform frequency encoding on the magnetic resonance signal of the excited slice.

The gradient coil driver 118 is used to provide a suitable power signal for each of the aforementioned three gradient coils in response to a sequence control signal sent by the controller unit 120.

The scanner 110 may further include a data acquisition unit 114. The data acquisition unit is used to acquire a magnetic resonance signal received by the radio frequency surface coil 119 or the body coil. The data acquisition unit 114 may include, for example, a radio frequency preamplifier (not shown), a phase detector (not shown), and an analog/digital converter (not shown), where the radio frequency preamplifier is used to amplify the magnetic resonance signal received by the radio frequency surface coil 119 or the body coil; the phase detector is used to perform phase detection on the amplified magnetic resonance signal; and the analog/digital converter is used to convert the phase-detected magnetic resonance signal from an analog signal to a digital signal. The data processing unit 130 can perform processing such as calculation and reconstruction on the digitized magnetic resonance signal so as to acquire a medical image.

The data processing unit 130 may include a computer and a storage medium, where a program of predetermined data processing to be executed by the computer is recorded on the storage medium. The data processing unit 130 may be connected to the controller unit 120 and perform data processing on the basis of the control signal received from the controller unit 120. The data processing unit 130 may also be connected to the data acquisition unit 114 to receive the magnetic resonance signal output by the data acquisition unit 114 so as to perform the aforementioned data processing.

The controller unit 120 may include a computer and a storage medium, where the storage medium is used to store a program executable by the computer, and when the computer executes the program, a plurality of components of the scanner 110 are enabled to implement operations corresponding to the aforementioned imaging sequence. The data processing unit 130 is also enabled to perform predetermined data processing.

The storage media of the controller unit 120 and the data processing unit 130 may include, for example, a ROM, a floppy disk, a hard disk, an optical disk, a magneto-optical disk, a CD-ROM, or a non-volatile memory card.

The controller unit 120 may be configured and/or arranged for use in different manners. For example, in some implementations, a single controller unit 120 may be used. In other implementations, a plurality of controller units 120 are configured to work together (for example, based on distributed processing configuration) or separately, where each controller unit 120 is configured to handle specific aspects and/or functions, and/or to process data used to generate a model used only for a specific medical imaging system 100. In some implementations, the controller unit 120 may be local (for example, in the same place as one or a plurality of medical imaging systems 100, for example, in the same facility and/or the same local network). In other implementations, the controller unit 120 may be remote and thus can only be accessed via a remote connection (for example, via the Internet or other available remote access technologies). In a specific implementation, the controller unit 120 may be configured in a manner similar to that of cloud technology, and may be accessed and/or used in a manner substantially similar to that of accessing and using other cloud-based systems.

The MRI system 100 further includes a test bed 140 on which the tested object 116 is placed. The tested object 116 may be moved into or out of the imaging space by moving the test bed 140 based on the control signal from the controller unit 120.

The MRI system 100 further includes an operation console unit 150 connected to the controller unit 120. The operation console unit 150 may send an acquired operation signal to the controller unit 120 so as to control operation statues of the aforementioned components of, for example, the test bed 140 and the scanner 110. The operation signal may include, for example, a scanning protocol and a parameter selected manually or automatically, where the scanning protocol may include the aforementioned imaging sequence. In addition, the operation console unit 150 may send the acquired operation signal to the controller unit 120 so as to control the data processing unit 130 in order to acquire a desired image.

The operation console unit 150 may include a user input device having a certain form of operator interface, such as a keyboard, a mouse, a voice activated controller, or any other suitable input devices, where an operator may input an operation signal/control signal to the controller unit 120 via the user input device.

The MRI system 100 may further include a display unit 160. The display unit 160 may be connected to the operation console unit 150 so as to display an operation interface, and may further be connected to the data processing unit 130 so as to display an image. In addition, the display unit 160 may be used to display an identified image quality type and a corresponding alarm signal.

In some embodiments, the system 100 may be connected to, via one or a plurality of configurable wired and/or wireless networks such as the Internet and/or a virtual private network, one or a plurality of display units, cloud networks, printers, workstations, and/or similar apparatuses located locally or remotely.

Figure 2:
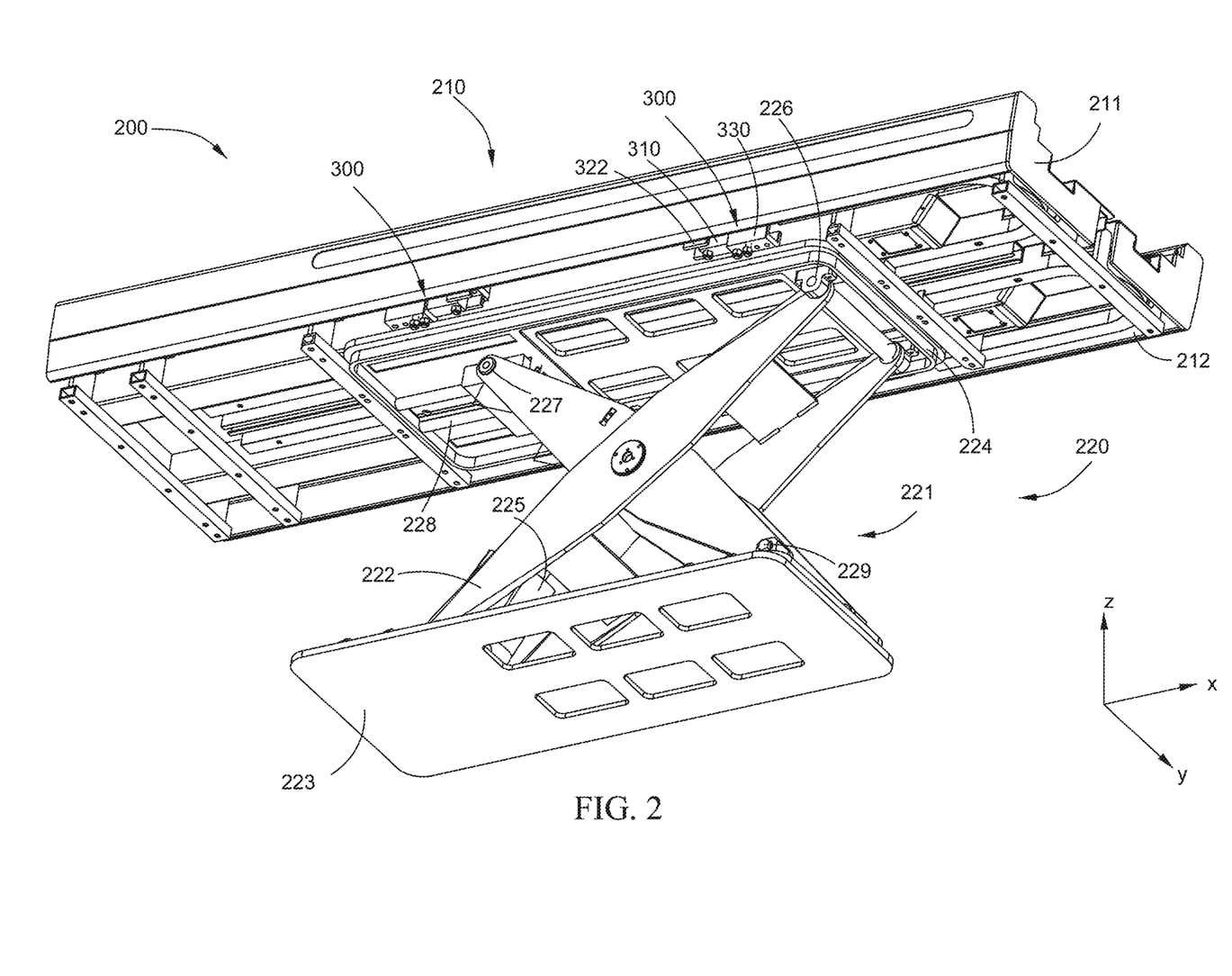
FIG. 2 is a perspective view of a test bed according to some embodiments of the present utility model.

FIG. 2 is a perspective view of a test bed 200 according to some embodiments of the present utility model. The test bed 200 is used to hold a patient so as to perform a medical imaging procedure. The test bed 200 may be used to hold and position the patient in different medical imaging systems, such as an X-ray system, a computed tomography system, a single photon emission computed tomography system, a positron emission tomography system, and a magnetic resonance imaging system. As shown in FIG. 2, the test bed 200 of some embodiments of the present utility model includes a support frame 210 used to bear a tested object, a base 220 used to support the support frame 210, and at least one weighing assembly 300, where the at least one weighing assembly 300 is fixed to the base 220 and acquires weight information of the tested object by sensing stress from the support frame 210.

In FIG. 2 to FIG. 6, an x-axis direction is defined as a lengthwise direction of the support frame 210 (a traveling direction of the test bed); a y-axis direction is defined as a widthwise direction of the support frame 210; and a z-axis direction is defined as a lifting direction of the test bed. The aforementioned directions are defined for ease of description.

In some embodiments, the support frame 210 includes a movement support frame 211 and a supporting support frame 212. During use, the test bed can be moved (along the x-axis direction) to be aligned with an entrance of a scanning cavity of a magnetic resonance scanning device. The movement support frame 211 can be driven by a driving assembly (not shown in the figure) to linearly reciprocate. For example, the movement support frame 211 may move towards or away from the main magnet along the direction of a central axis of the main magnet of the magnetic resonance imaging system so as to position the tested object in a position required for imaging. The supporting support frame 212 is used to support the movement support frame

211. When the movement support frame 211 linearly reciprocates, the supporting support frame 212 is in a stationary state.

In some embodiments, the base 220 includes a lifting assembly 221 and a top plate 224 and a bottom plate 223 connected to the lifting assembly 221. The lifting assembly 221 may be connected to the top plate 224 and the bottom plate 223 by a pivot joint 226 and/or a roller assembly 227. For example, one end of the lifting assembly 221 is connected to the top plate 224 by the pivot joint 226; the other end of the lifting assembly 221 is connected to the top plate 224 by the roller assembly 227; and the roller assembly 227 may engage with a guide rail 228 mounted on a lower surface of the top plate 224. Similarly, one end of the lifting assembly 221 is connected to the bottom plate 223 by a pivot joint 229; the other end of the lifting assembly 221 is connected to the bottom plate 223 by a roller assembly (not shown); and the roller assembly may engage with a guide rail (not shown) mounted on an upper surface of the bottom plate 223.

The lifting assembly 221 includes a lifting unit 222 and a driving unit 225. The lifting unit 222 can be driven by the driving unit 225 to move relatively, so that the test bed 200 achieves a raised configuration and a lowered configuration. Specifically, the driving unit 225 may include one or a plurality of a telescopic driving unit, a hydraulic driving unit, a pneumatic driving unit, an electro-hydraulic driving unit, and any other driving unit.

The test bed 200 of some embodiments of the present utility model may include at least one weighing assembly 300. Optionally, the test bed 200 includes a plurality of weighing assemblies 300, and the plurality of weighing assemblies 300 are fixed between the support frame 210 and an upper surface of the base 220. Specifically, the plurality of weighing assemblies 300 are fixed between the support frame 210 (the supporting support frame 212) and the top plate 224 in the base 220. In some non-limiting embodiments, the test bed 200 includes four weighing assemblies 300 positioned along the x-axis direction and symmetrical about a center, where the center is the center of gravity of the support frame 210.

Although FIG. 2 shows only two weighing assemblies, those skilled in the art can understand that another two weighing assemblies are present on the other side of the support frame 210 and the top plate 224. In addition, although the embodiment shown in FIG. 2 includes four weighing assemblies, those skilled in the art can understand that the number of weighing assemblies is not limited, and can be configured or adjusted according to actual requirements. For example, only one weighing assembly may be provided, or two or eight or other numbers of weighing assemblies may be provided.

Figure 3:
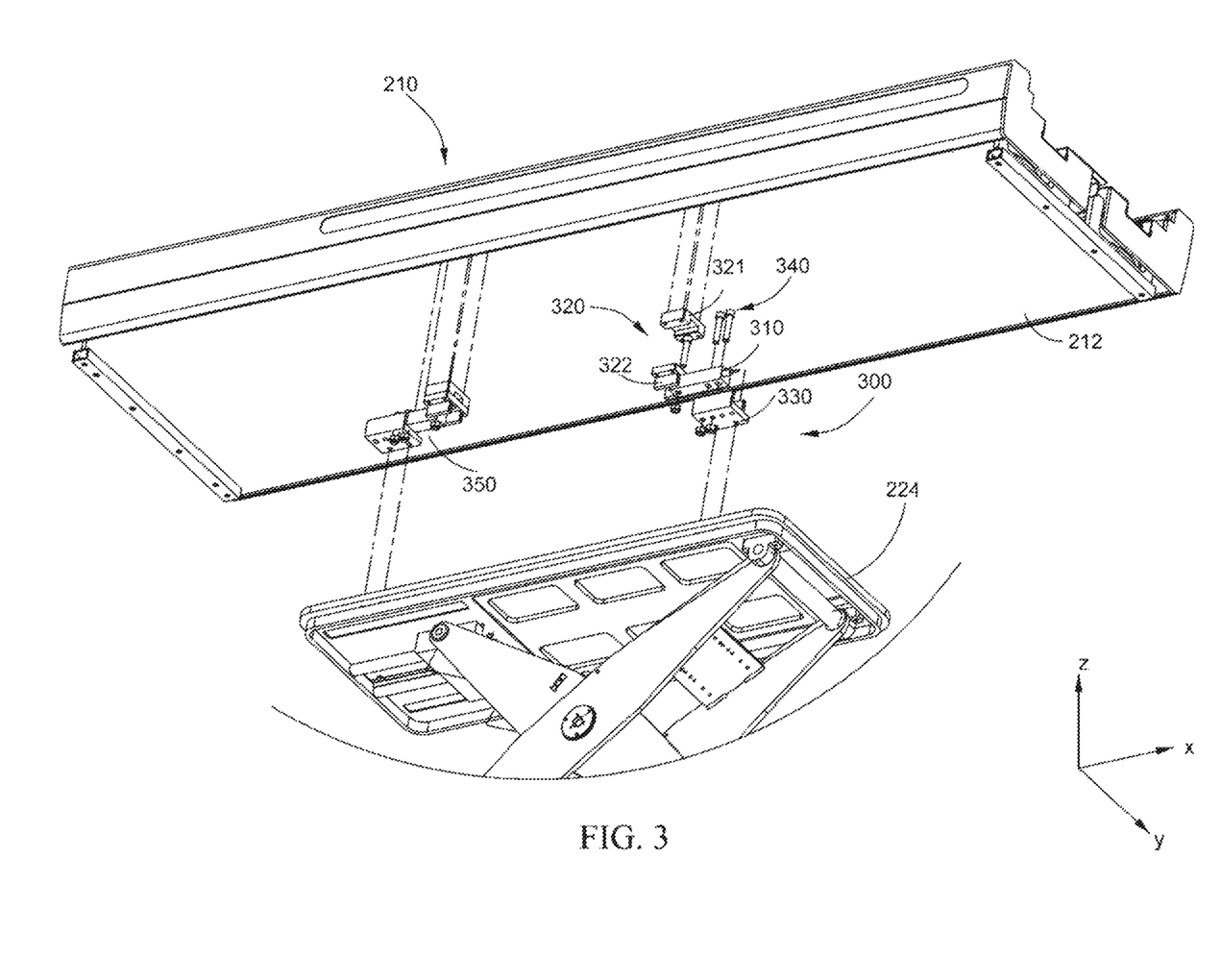
FIG. 3 is a partial exploded view of the test bed shown in FIG. 2.
Figure 4:
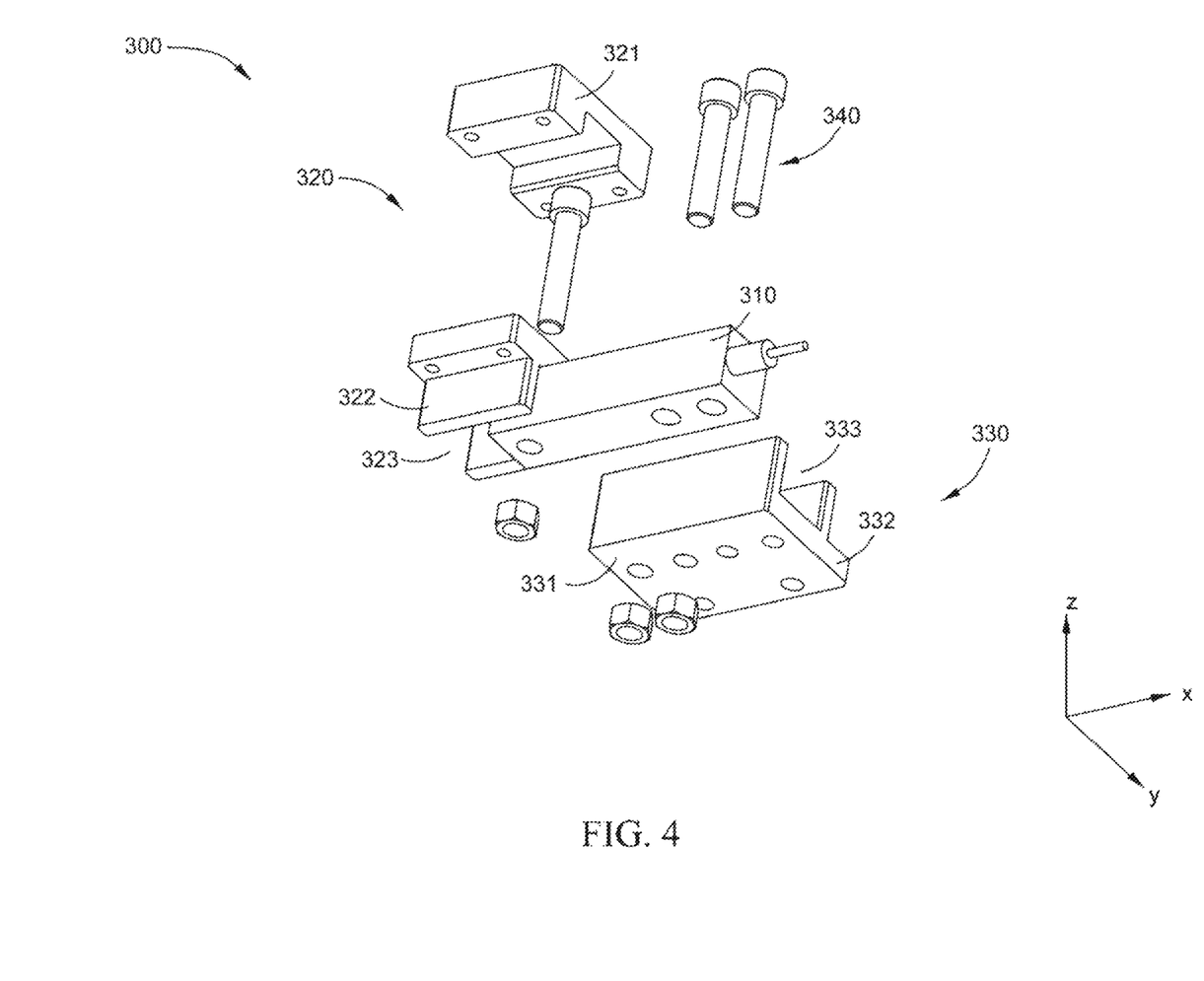
FIG. 4 is an exploded view of a weighing assembly in the test bed shown in FIG. 2.

FIG. 3 shows a partial exploded view of the test bed 200 shown in FIG. 2, and FIG. 4 shows an exploded view of the weighing assembly 300 in the test bed 200 shown in FIG. 2. For clear illustration, structures on a lower surface of the supporting support frame 212 are omitted in FIG. 3. As shown in FIGS. 3 and 4, the weighing assembly 300 further includes a sensor unit 310 used to sense the stress from the support frame 210.

In some embodiments, the sensor unit 310 may include a single-ended beam load cell. Specifically, the single-ended beam load cell can convert stress applied thereto into a measurable electrical signal. Therefore, the weighing assembly needs to include an apparatus for transmitting force from the support frame to the sensor unit. In addition, the sensor unit needs to be fixed, and a deformation space is required. In this case, the load cell can deform so as to acquire the weight information of the tested object. In some embodiments, the sensor unit 310 is positioned along the x-axis direction.

In some embodiments, the weighing assembly 300 further includes a force transmission apparatus 320 used to transmit the stress from the support frame 210 to the sensor unit 310. The force transmission apparatus 320 is mounted on an upper side of the sensor unit 310. Specifically, an upper side of the force transmission apparatus 320 is fixed to the lower surface of the supporting support frame 212.

In some embodiments, the force transmission apparatus 320 includes a first component 321 and a second component 322. A recess 323 used to accommodate the sensor unit 310 is provided on the second component 322 (along the x-axis direction) so as to better fix the sensor unit 310. The first component 321 is provided above the second component 322 so as to better transmit the stress to the sensor unit 310. In some embodiments, a part of the recess 323 contacts the sensor unit 310 so as to better transmit the stress to the sensor unit 310. In some embodiments, a recess may not be provided on the second component 322, and the force transmission apparatus is fixed above the sensor unit by means of a connection component (such as a nut).

In some embodiments, when the test bed 200 includes a plurality of weighing assemblies, the force transmission apparatuses of the plurality of weighing assemblies are also symmetrical about a center (the center of gravity of the support frame 210).

Although FIGS. 3 and 4 show that the force transmission apparatus 320 includes two components (321 and 322), those skilled in the art can understand that the force transmission apparatus 320 may include any number of components in any shape as long as the force transmission apparatus 320 can apply the force from the support frame to the sensor unit 310. In addition, although the force transmission apparatus 320 includes the first component 321 and the second component 322, those skilled in the art can understand that the force transmission apparatus 320 may also be integrally formed, that is, the first component 321 and the second component 322 are one integrally formed component.

In some embodiments, the weighing assembly 300 further includes a fixing apparatus 330 used to fix and support the sensor unit 310. The fixing apparatus 330 is mounted on a lower side of the sensor unit 310. A deformation space 350 (as shown in FIG. 3) is formed in a position on the lower side of the sensor unit 310 opposite the force transmission apparatus 320. The deformation space 350 allows the sensor unit 310 to deform along the direction of the stress (the z-axis direction).

In some embodiments, the fixing apparatus 330 includes a main body portion 331 and an extension portion 332 extending along the main body portion 331. The main body portion 331 is configured to include a recess 333 used to accommodate the sensor unit 310. Further, a part of the recess 333 contacts the sensor unit 310. The extension portion 332 is fixed to the top plate 224, so that the main body portion 331 can be partially suspended. In some embodiments, the extension portion 332 in the fixing apparatus 330 extends, in an inward direction, along the main body portion, where the inward direction is defined as a direction toward the center of the support frame.

In some embodiments, the weighing assembly 300 further includes a connection component 340, and each of the sensor unit 310, the force transmission apparatus 320, and the fixing apparatus 330 includes at least one through-hole.

The connection component 340 may pass through the at least one through-hole for fixing the sensor unit 310, the force transmission apparatus 320, and the movement support frame 310, as well as the sensor unit 310, the fixing apparatus 330, and the top plate 224.

Figure 5:
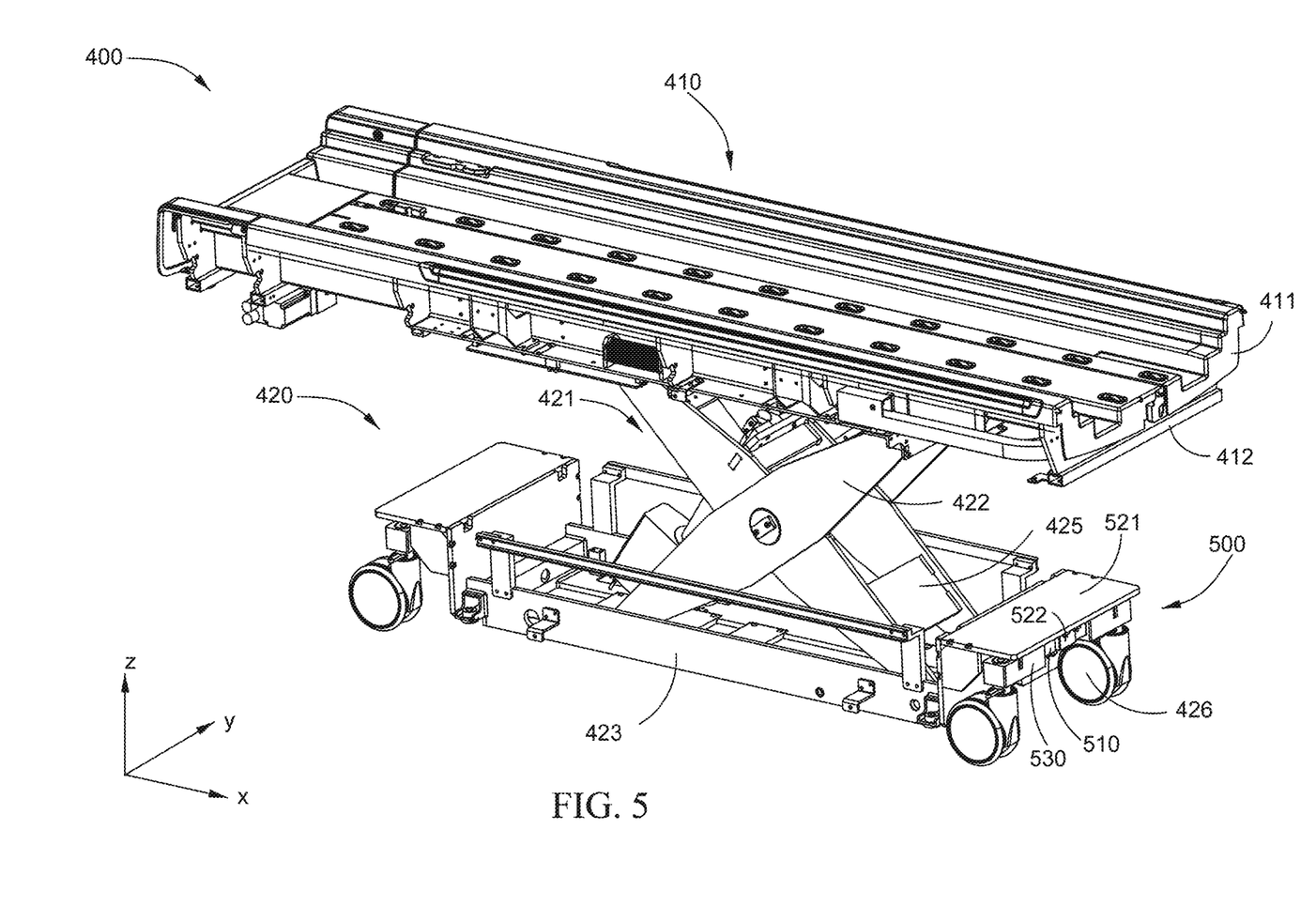
FIG. 5 is a perspective view of a test bed according to other embodiments of the present utility model.

FIG. 5 shows a test bed 400 according to some embodiments of the present utility model. As shown in FIG. 5, different from the test bed 200 shown in FIG. 2, the test bed 400 further includes a movement assembly 426 provided at the bottom of the test bed 400. Specifically, the movement assembly 426 includes two movement wheels positioned at one end of the bottom (such as a bottom plate 423) of a base 420 and two movement wheels positioned at the other end of the bottom of the base 420.

In some embodiments, the test bed 400 includes a plurality of weighing assemblies 500. The plurality of weighing assemblies are fixed to the movement assembly 426. Specifically, the test bed 400 includes two weighing assemblies 500, and each weighing assembly 500 is fixed to two adjacently positioned movement wheels.

Figure 6:
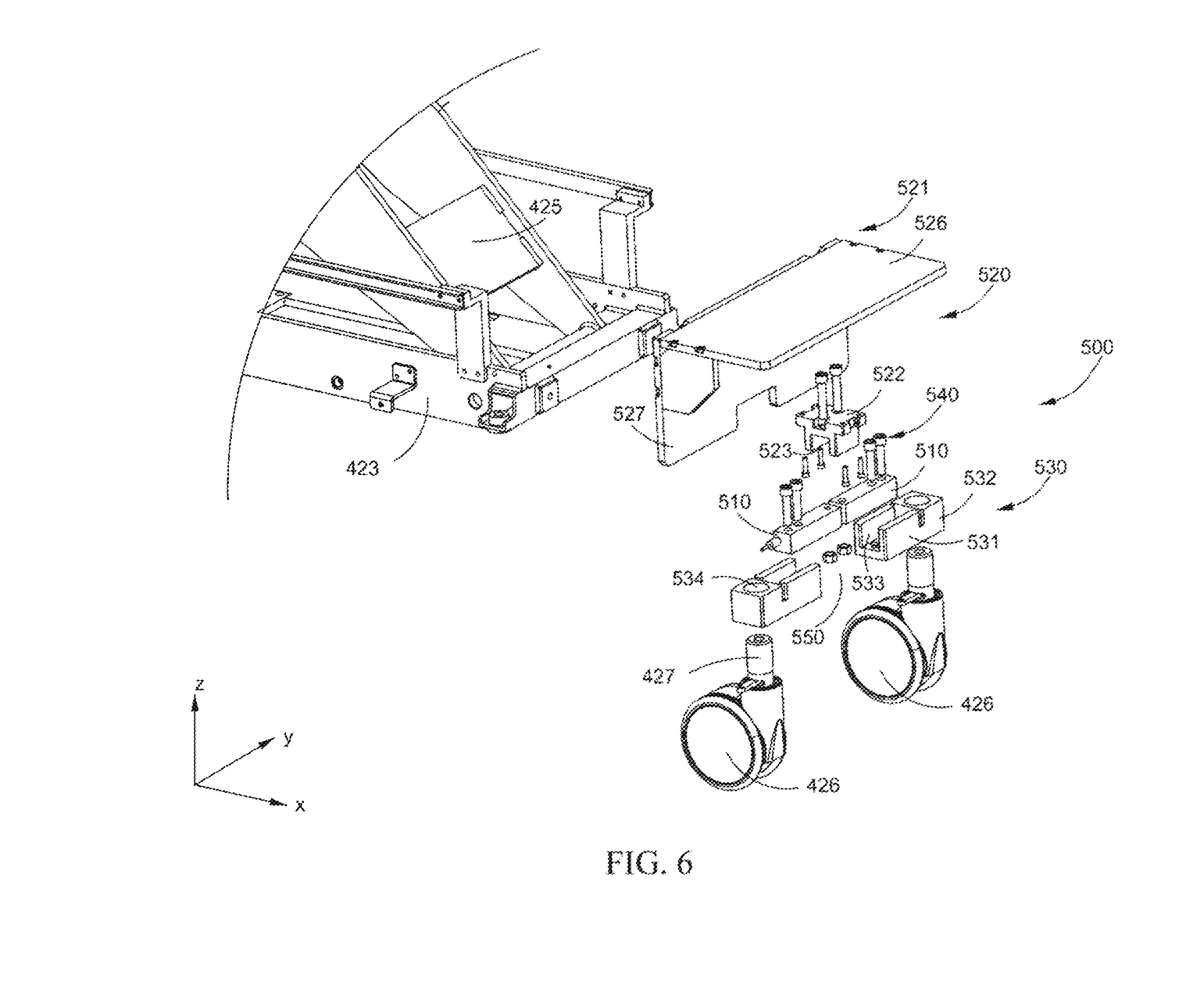
FIG. 6 is a partial exploded view of the test bed shown in FIG. 5.

FIG. 6 shows an exploded view of the weighing assembly 500 in the test bed 400 shown in FIG. 5. As shown in FIG. 6, the weighing assembly 500 includes a sensor unit 510 used to sense stress from a support frame 410. Specifically, the weighing assembly 500 includes two sensor units 510. The weighing assembly 500 is easily mounted on the movement assembly, and the weighing assemblies 500 are symmetrical about a center. In some embodiments, the two sensor units 510 are positioned along the y-axis direction.

Although the weighing assembly 500 shown in FIG. 6 includes two sensor units 510, those skilled in the art can understand that the number of sensor units is not limited to two, and the weighing assembly can include any number of sensor units. For example, the weighing assembly may include one sensor unit provided between two movement wheels.

In some embodiments, the sensor unit 510 is a single-ended beam load cell. Specifically, the single-ended beam load cell can acquire a measurable electrical signal by means of stress applied to the single-ended beam load cell. Therefore, the weighing assembly needs to include an apparatus for transmitting force from the support frame to the sensor unit. In addition, the sensor unit needs to be fixed, and a deformation space is required. In this case, the load cell can deform so as to acquire the weight information of the tested object.

In some embodiments, the weighing assembly 500 further includes a force transmission apparatus 520 used to transmit the stress from the support frame 410 to the sensor unit 510. The force transmission apparatus 520 is mounted on an upper side of the sensor unit 510. Specifically, the force transmission apparatus 520 is fixed to an end portion of the bottom plate 423.

In some embodiments, the force transmission apparatus 520 includes a first component 521 and a second component 522. The second component 522 includes a recess 523 used to accommodate the sensor unit 510 so as to fix the sensor unit 510. The first component 521 includes a main body portion 526 fixed above the second component 522 and an extension portion 527 configured to be perpendicular to the main body portion 526. The extension portion 527 includes at least one through-hole (not shown in the figure) for connection to the bottom plate 423. The main body portion 526 is used to transmit the stress of the support frame 410 to the sensor unit 510 via the bottom plate 423 and the extension portion 527. In some embodiments, the force transmission apparatus 520 includes only one second component 522. The second component 522 is connected to both the two sensor units 510. Specifically, the second component includes two through-holes, and the two through-holes are respectively used to fix the two sensor units. In some embodiments, the extension portion 527 and the main body portion 526 are integrally formed. In other embodiments, the extension portion 527 and the main body portion 526 are assembled together.

Although FIG. 6 shows that the force transmission apparatus 520 includes two components (521 and 522), those skilled in the art can understand that the force transmission apparatus 520 may include any number of components in any shape as long as the force transmission apparatus 520 can apply the force from the support frame to the sensor unit 510. In addition, although the force transmission apparatus includes the first component 521 and the second component 522, those skilled in the art can understand that the force transmission apparatus may also be integrally formed. That is, the first component 521 and the second component 522 are one integrally formed component.

In some embodiments, the weighing assembly 500 further includes a fixing apparatus 530 used to fix and support the sensor unit 510. The fixing apparatus 530 is mounted on a lower side of the sensor unit 510. A deformation space 550 is formed in a position on the lower side of the sensor unit 510 opposite the force transmission apparatus 520. The deformation space 550 allows the sensor unit 510 to deform along the direction of the stress.

In some embodiments, the fixing apparatus 530 includes a main body portion 531 used to fix the sensor unit 510, and a recess 533 used to accommodate the sensor unit 510 is provided on the main body portion 531. Further, the weighing assembly 500 includes two fixing apparatuses 530, and each fixing apparatus includes a recess 533 used to accommodate the sensor unit 510. In addition, the fixing apparatus 530 further includes an extension portion 532 extending along the main body portion 531 (the y-axis direction). The extension portion 532 includes a through-hole 534. The through-hole 534 may be configured to receive or fix a protrusion portion 427 of the movement assembly 426 so as to fix and/or mount the movement wheel 426.

In some embodiments, the weighing assembly 500 further includes a connection component 540. The connection component 540 is used to fix the sensor unit 510, the force transmission apparatus 520, and the bottom plate 420 and to fix the sensor unit 510, the fixing apparatus 530, and the movement assembly 426.

Although the embodiments shown in FIGS. 5 and 6 disclose that the weighing assembly is provided on the movement assembly of the movable test bed, those skilled in the art can understand that in the movable test bed (that is, the movement assembly is provided on the base), the weighing assembly can also be provided between the base and the support frame, as in the embodiments shown in FIGS. 2-4.

Figure 7:
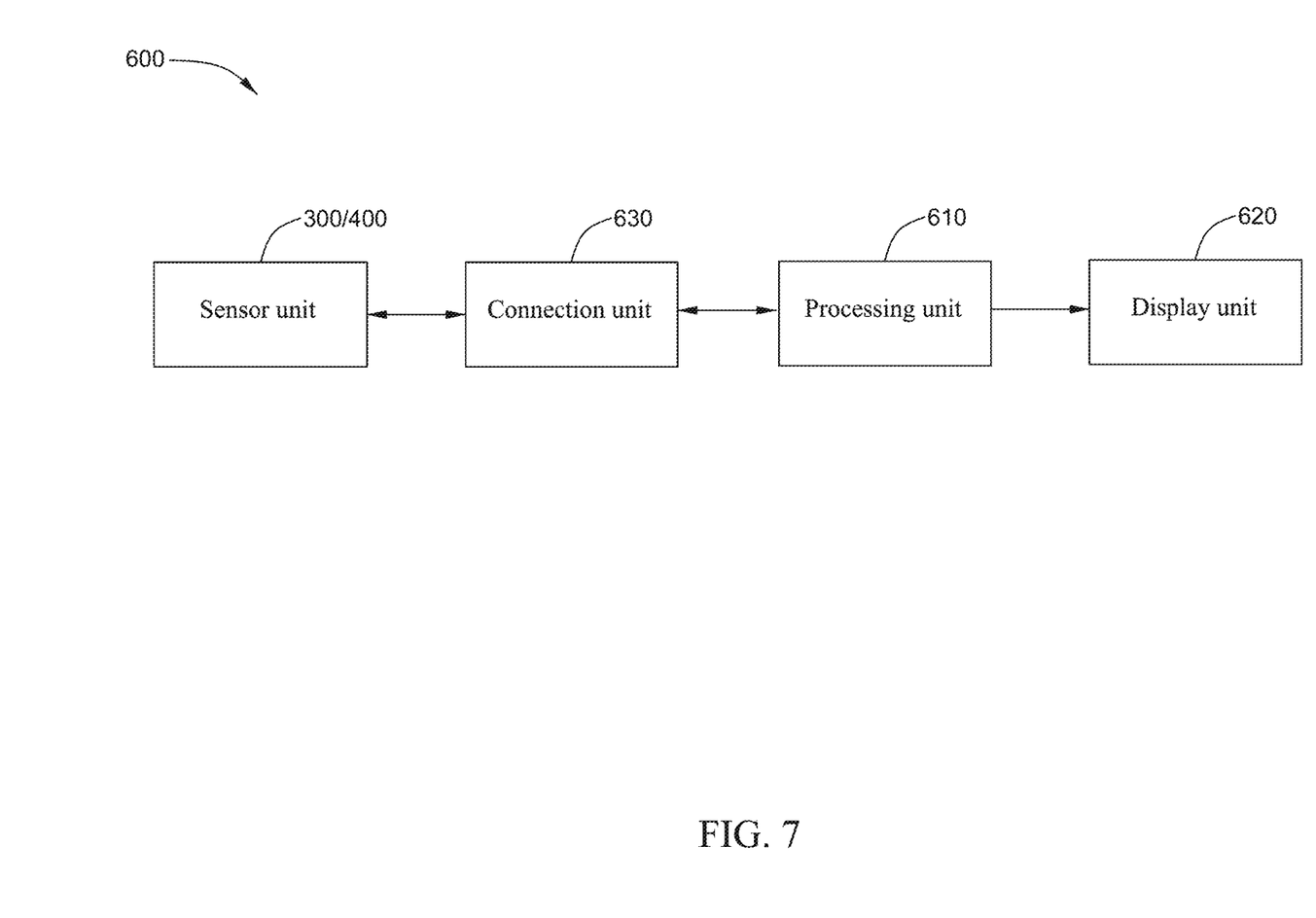
FIG. 7 shows a schematic diagram of a control apparatus in a medical imaging system.

FIG. 7 shows a schematic diagram of a control apparatus 600 of a medical imaging system. As shown in FIG. 7, the control apparatus 600 includes a connection unit 630. The connection unit 630 is connected to the weighing assembly 300/500 (i.e., the sensor unit 310/610), and is used to receive a measurement signal sent by the sensor unit 310/610. Specifically, the connection unit 630 is electrically connected to the sensor unit 310/610, and the connection unit 630 includes a circuit board so as to receive the (analog) measurement signal sent by the sensor unit. In some embodiments, the connection unit 630 includes an adjustable resistor module. The resistance of the adjustable resistor module is changed so that a weighing parameter of the sensor unit 310/610 is changed so as to calibrate (or correct) the sensor unit. The resistance of the connection unit is adjusted so as to calibrate the sensor unit, thereby reducing the complexity of maintenance and calibration. In some embodiments, the adjustable resistor module includes a rotary resistor.

The control apparatus 600 further includes a processing unit 610. The processing unit 610 is connected to the connection unit 630 and is used to perform calculation on a measurement signal from the connection unit 630 so as to acquire weight information of a tested object. Specifically, the processing unit 610 includes an analog-to-digital conversion module. The analog-to-digital conversion module is used to convert the analog signal measured by the sensor unit into a digital signal for calculation. In addition, the processing unit 610 further includes a calculation module. The calculation module is used to sum digital signals corresponding to values measured by the plurality of sensor units so as to acquire the weight information of the tested object.

In some embodiments, the sensor unit in the weighing assembly is not limited to the load cell disclosed in the present utility model, and may be a sensor of another type. Therefore, the calculation module in the processing unit may also perform, by other means instead of summation, calculation on the values measured by the sensor units.

In some embodiments, the control apparatus 600 further includes a display unit 620. The display unit 620 is connected to the processing unit 610 and is used to display the weight information of the tested object. In some embodiments, the weight information of the tested object is displayed in the display unit 620, so that a doctor may determine scanning time and/or scanning intensity on the basis of the weight information. In other embodiments, the controller unit (or the processing unit) of the MRI system may automatically determine scanning time and/or scanning intensity on the basis of the weight information.

In addition, the sensor unit may send measurement information to the processing unit 610 in real time, that is, the processing unit 610 may acquire real-time weight information of the tested object, so that the doctor (or the MRI system) can analyze and/or acquire the condition of the tested object on the basis of the real-time weight information.

Figure 8:
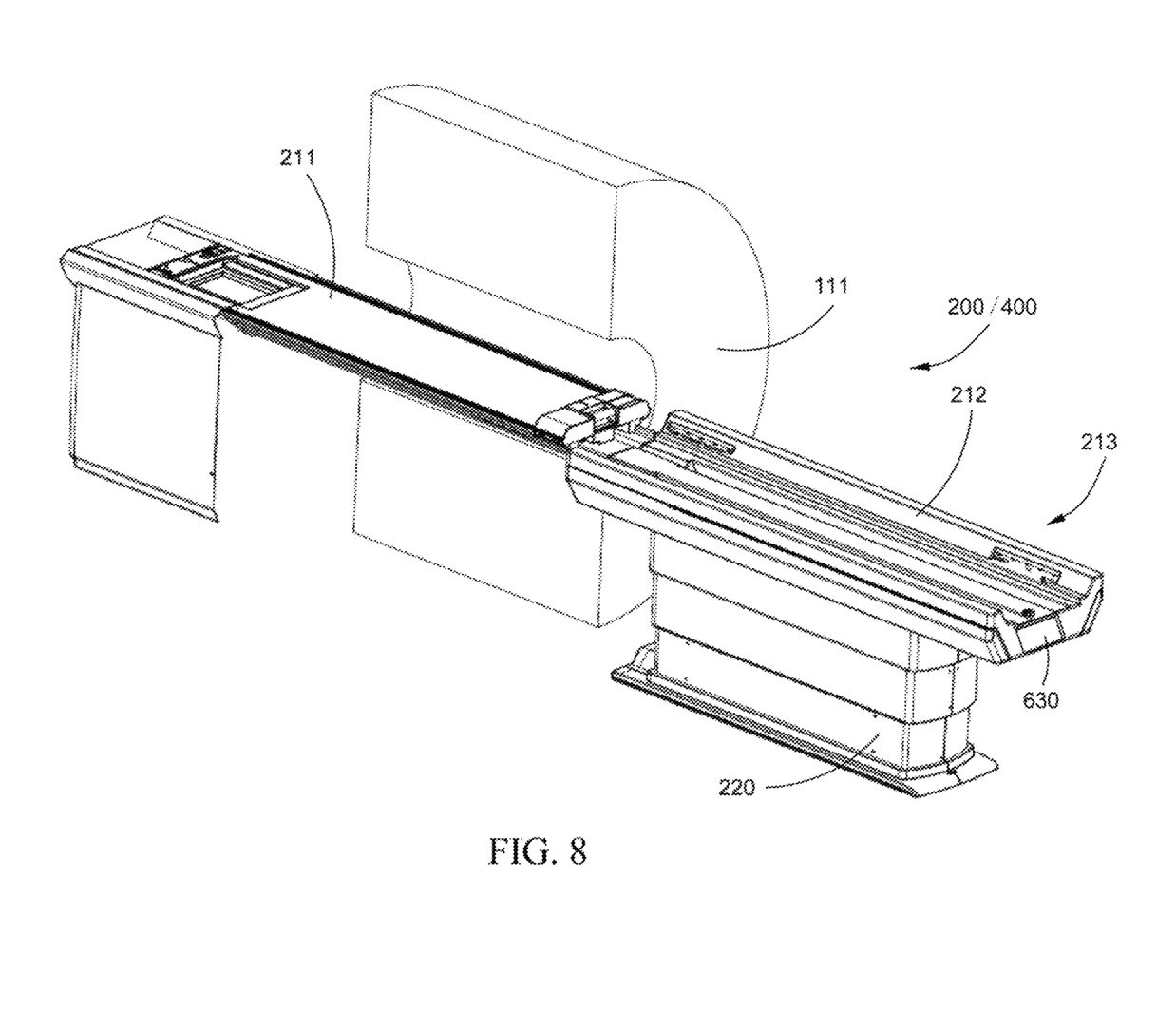
FIG. 8 shows a schematic diagram of the position of a connection unit in a medical imaging system.

FIG. 8 shows a schematic diagram of the position of the connection unit in the medical imaging system. As shown in FIG. 8, when the medical imaging system is the MRI system 100 shown in FIG. 1, the MRI system includes the main magnet 111 and the test bed 200/400 (i.e., the 140 in FIG. 1), and further includes the weighing assembly provided in the test bed 200/400, such as the weighing assembly 300 provided between the base and the support frame shown in FIG. 2 or the weighing assembly 500 provided on the movement assembly of the base shown in FIG. 5. In some embodiments, the MRI system further includes the connection unit 630. The connection unit 630 is connected to at least one weighing assembly 300/500 in the test bed 200/400. The weighing assembly 300/500 includes the sensor unit 310/510. The connection unit 630 includes a circuit board so as to receive the measurement signal sent by at least one sensor unit. Optionally, the connection unit 630 is electrically connected to the sensor unit 310/510 and is used to supply power to the sensor unit 310/510.

In some embodiments, the connection unit 630 is positioned away from the main magnet 111. For example, the connection unit 630 may be provided at an end 213 of the test bed 200/400 located away from the main magnet 111 so as to reduce the influence thereof on image quality. Specifically, the connection unit 630 may be mounted on an end portion of the support frame (or the supporting support frame 212) located away from the main magnet 111. Optionally, the connection unit 630 may also be mounted on an end portion of the base 220 located away from the main magnet 111, or the connection unit 630 may also be mounted on a lower surface of the supporting support frame 212 located away from the main magnet 111. Optionally, the connection unit 630 may also be provided in a control room of the MRI system.

Although FIG. 8 shows that the connection unit 630 is provided at the end portion of the supporting support frame, those skilled in the art can understand that the position of the connection unit 630 is not limited to only the end portion of the supporting support frame. The connection unit 630 may also be provided in a position located away from the main magnet so as to reduce the influence of the connection unit on a magnetic field and image quality.

The MRI system shown in FIG. 8 further includes a processing unit (not shown in the figure). The processing unit is connected to the connection unit 630 and is used to perform calculation on the measurement signal from the connection unit 630 so as to acquire the weight information of the tested object. In some embodiments, the processing unit is connected to the controller unit 120 (or the data processing unit 130) in the MRI system 100 shown in FIG. 1, or serves as a part of the controller unit 120 (or the data processing unit 130) and is used to receive and perform calculation on the measurement value from the sensor unit 310/510 so as to acquire the weight information of the tested object.

The MRI system shown in FIG. 8 further includes a display unit (not shown in the figure). The display unit may be connected to the processing unit, and is used to display the weight information of the tested object. In some embodiments, the display unit is the display unit 160 in the MRI system 100 shown in FIG. 1.

Therefore, that is, the control apparatus shown in FIG. 7 may be provided separately. For example, the control apparatus is integrated on the test bed and is communicatively connected to the controller unit of the medical imaging system. Alternatively, the connection unit may be provided in the test bed or the control room, and the connection unit is configured to be communicatively connected to the controller unit and/or the display unit of the medical imaging system (such as the MRI system), so that the controller unit and/or the display unit includes the functions of the processing unit 610 and/or the display unit 620.

The weighing assembly provided by the present utility model is provided in the test bed of the MRI system. The stress applied by the tested object through the support frame is sensed, so that the weight information of the tested object is acquired. The force transmission apparatus is provided on the upper side of the sensor, so that the force of the support frame is better transmitted to the sensor unit. The fixing apparatus is provided on the lower side of the sensor, and the deformation space is formed in the position on the lower side of the sensor opposite the transmission apparatus, so that the sensor is allowed to deform along the direction of the stress, and the weight of the tested object is accurately measured. In addition, the connection unit is provided in the control apparatus, and resistors respectively corresponding to the sensors are provided in the connection unit, so that the resistance of the resistor may be changed to change the weighing parameter of the sensor so as to calibrate the sensor, thereby avoiding the problem in which only control software in the MRI system can modify the weighing parameter of the sensor, and reducing maintenance costs and time. Furthermore, application of the weighing assembly is not limited to a test bed of an MRI system, and the weighing assembly is also applicable to other medical imaging systems such as a CT system, an X-ray imaging system, etc.

Some exemplary embodiments have been described above; however, it should be understood that various modifications may be made. For example, if the described techniques are performed in a different order and/or if the components of the described system, architecture, apparatus, or circuit are combined in other manners and/or replaced or supplemented with additional components or equivalents thereof, then a suitable result can be achieved. Accordingly, other implementation manners also fall within the protection scope of the claims.

The invention claimed is:

1. A test bed, comprising:
a support frame, used to bear a tested object;
a base, used to support the support frame;
at least one weighing assembly, fixed to the base and acquiring weight information of the tested object by sensing stress from the support frame;
wherein the weighing assembly comprises a sensor unit used to sense the stress from the support frame;
wherein the weighing assembly further comprises a force transmission apparatus used to transmit the stress from the support frame to the sensor unit, and the force transmission apparatus is mounted on an upper side of the sensor unit;
wherein the weighing assembly further comprises a fixing apparatus used to fix and support the sensor unit; the fixing apparatus is mounted on a lower side of the sensor unit; a deformation space is formed in a position on the lower side of the sensor unit opposite the force transmission apparatus; and the deformation space allows the sensor unit to deform along the direction of the stress; and
wherein the fixing apparatus includes a main body portion and an extension portion extending along the main body portion and wherein the main body portion is configured to include a recess to accommodate the sensor unit.

2. The test bed according to claim 1, wherein the sensor unit is a single-ended beam load cell.

3. The test bed according to claim 1, wherein the test bed comprises a plurality of weighing assemblies, and the plurality of weighing assemblies are fixed between the support frame and an upper surface of the base.

4. The test bed according to claim 3, wherein the test bed comprises four weighing assemblies symmetrical about a center, and the center is the center of gravity of the support frame.

5. A medical imaging system, the medical imaging system comprising the test bed according to claim 1 and a control apparatus.

6. The medical imaging system according to claim 5, wherein the control apparatus comprises:
a connection unit, connected to at least one weighing assembly, wherein the at least one weighing assembly comprises at least one sensor unit, and the connection unit is used to receive a measurement signal sent by the at least one sensor unit.

7. The medical imaging system according to claim 6, wherein the connection unit comprises an adjustable resistor module, and the resistance of the adjustable resistor module is changed so that a weighing parameter of the at least one sensor unit is changed.

8. The medical imaging system according to claim 6, wherein the control apparatus further comprises:
a processing unit, connected to the connection unit and used to perform calculation on the measurement signal from the connection unit so as to acquire weight information of a tested object.

9. The medical imaging system according to claim 8, wherein the control apparatus further comprises:
a display unit, connected to the processing unit and used to display the weight information of the tested object.

10. The medical imaging system according to claim 8, wherein the weight information is a real time weight information of the tested object and wherein the processing system uses weight information of the tested object to determine scanning time, scanning intensity or both during scanning performed on the tested object.

11. A magnetic resonance imaging system, the magnetic resonance imaging system comprising a main magnet and the test bed according to claim 1.

12. The magnetic resonance imaging system according to claim 11, wherein the magnetic resonance imaging system comprises:
a connection unit, connected to at least one weighing assembly in the test bed, wherein the at least one weighing assembly comprises at least one sensor unit, and the connection unit is used to receive a measurement signal sent by the at least one sensor unit.

13. The magnetic resonance imaging system according to claim 12, wherein the connection unit is positioned away from the main magnet.

14. The magnetic resonance imaging system according to claim 13, wherein the connection unit is provided at an end of the test bed located away from the main magnet.

15. The magnetic resonance imaging system according to claim 12, wherein the connection unit comprises an adjustable resistor module, and the resistance of the adjustable resistor module is changed so that a weighing parameter of the at least one sensor unit is changed.

16. A test bed, comprising:
a support frame, used to bear a tested object;
a base, used to support the support frame;
at least one weighing assembly, fixed to the base and acquiring weight information of the tested object by sensing stress from the support frame;
wherein the base further comprises a movement assembly provided at the bottom of the base, and the weighing assembly is fixed to the movement assembly;
wherein the movement assembly comprises two movement wheels positioned at one end of the bottom of the base and two movement wheels positioned at the other end of the bottom of the base; the test bed comprises two weighing assemblies; and each weighing assembly is fixed to two adjacently positioned movement wheels; and
wherein the weighing assembly comprises two sensor units, and the sensor units are respectively fixed to the movement wheels.

* * * * *